(12) United States Patent
Prell (10) Patent No.: US 6,777,394 B1
(45) Date of Patent: Aug. 17, 2004

(54) METHODS AND COMPOSITIONS FOR REGULATING IMIDAZOLINE RECEPTORS

(76) Inventor: George D. Prell, 17 Fairmount Ave., Upper Montclaire, NJ (US) 07043-2404

( * ) Notice: Subject to any disclaimer, the term of this patent is extended or adjusted under 35 U.S.C. 154(b) by 0 days.

(21) Appl. No.: 09/353,670

(22) Filed: Jul. 15, 1999

Related U.S. Application Data (60) Provisional application No. 60/092,945, filed on Jul. 15, 1998.

(51) Int. Cl.[7] .......................... A01K 43/04; A61K 31/70
(52) U.S. Cl. .................. 514/43; 536/26.9; 530/388.21; 530/388.22; 435/6; 435/7.2; 435/7.9
(58) Field of Search ...................... 530/388.22, 388.21; 514/43; 536/26.9; 435/6, 7.2, 7.9

(56) References Cited

U.S. PATENT DOCUMENTS 5,681,947 A * 10/1997 Bergstrom et al.

OTHER PUBLICATIONS

Tabor and Hayaishi, 1955, J. American Chem. Soc. 77:505–50611.
Karjala SA, 1955, J. Amer. Chem. Soc. 77:504–505.
Karjala SA, 1956, J. Biol. Chem. 219:9–12.
Bauer, 1958, BBA 30:219.
Baddiley et al., 1958, J. Chem Soc. 3743–3745.
Bauer, 1962, J. Org. Chem 27:167–170.
Crowley GM, 1964, J. Biol. Chem. 239:2593–2601.
Robinson J.D. and Green, 1964, Nature 203: 1178–1179.
Beaven MA et al., 1974, Europ. J. Pharmacol. 29:138–146.
Moss J et al., 1976, J. Clin Invest 58:137–141.
Beaver MA et al., 1976, Experientia 32:1180–1182.
Atlas, D et al. 1987, J. Cardiovascular Pharmacol. 10 (suppl. 1.12) S122–5127.
Atlas D. 1991, Biochemical Pharmacology 41:1541–1549.
Matulic–Adamic, 1991, Korean J. Med. Chem 1:54–64.
Thomas and Prell, 1993, Soc. Neurosci Abstr 19:85.
Li, G et al., 1994, Science 263:966–968.
Emsberger P. et al., 1995, FASEB J. 9:A114.
Thomas and Prell, 1995, J. Neurochem. 65:818–826.
Thomas et al., 1995, Soc. Neurosci. Abst. 21:1857.
Atlas D, 1995, Annals of the New York Academy of Sciences 783:314 324.
Morgan et al., 1995, Ann. N.Y. Acad. Sci 763:361–373.
Regunathan and Reis 1996, Ann. Dev. Pharmacol Toxicol 36:511–44.
Emsberger P. et al., 1997, J. Hypertension 15:59–523.
Chan et al., 1997, Brit. J. Pharmacol 120:926–932.
Eglen RM, 1998, Trends in Pharmacol.Sci; 19:381–390.

* cited by examiner

Primary Examiner—James O. Wilson
Assistant Examiner—Patrick Lewis
(74) Attorney, Agent, or Firm—Baker Botts L.L.P.

(57) ABSTRACT

The present invention relates to methods and compositions for regulating the activity of imidazoline receptors. In particular, the invention relates to pharmaceutical compositions comprising imidazoleacetic acid-ribotide (IAA-RP), imidazoleacetic acid-riboside (IAA-R) and its related congeners such as pros-linked ribotide and riboside. The invention is based on the discovery that IAA-RP and to a lesser extent IAA-P bind with a high affinity to imidazoline receptors. Antibodies to IAA-RP, IAA-R are additionally provided, as well as screening methods for identification of compounds that either promote or antagonize the activity of IAA-RP, IAA-R and its related congeners. The invention further relates to diagnostic and prognostic methods for detection of abnormalities in levels or activity of IAA-RP and IAA-R. The invention encompasses treatment of disorders related to the imidazoline system, including hypertension, glaucoma, psychiatric (e.g., depression), neurological (e.g., motor disorders, neurodegenerative disorders), diabetes and disorders related to platelet aggregation.

11 Claims, 4 Drawing Sheets

R=H, R'=PO₃H₂  IMIDAZOLEACETIC ACID-RIBOTIDE
R=R'=H  IMIDAZOLEACETIC ACID-RIBOSIDE

METHODS AND COMPOSITIONS FOR REGULATING IMIDAZOLINE RECEPTORS

This application claims the benefit of Provisional application Ser. No. 60/092,945, filed Jul. 15, 1998.

1. INTRODUCTION

The present invention relates to methods and compositions for regulating the activity of imidazoline receptors. In particular, the invention relates to pharmaceutical compositions comprising imidazoleacetic acid-ribotide (IAA-RP) and imidazoleacetic acid-riboside (IAA-R). The invention is based on the discovery that IAA-RP and to a lesser extent IAA-R bind with a high affinity to imidazoline receptors. Antibodies to IAA-RP and IAA-R are additionally provided, as well as screening methods for identification of compounds that either promote or antagonize the activity of IAA-RP and IAA-R. The invention further relates to diagnostic and prognostic methods for detection of abnormalities in levels or activity of IAA-RP and IAA-R. The invention encompasses treatment of disorders related to the imidazoline system, including hypertension, glaucoma, psychiatric (e.g., depression), neurological (e.g., motor disorders, neurodegenerative disorders), diabetes and disorders related to platelet aggregation.

2. BACKGROUND OF THE INVENTION

Imidazoline receptors are now generally recognized as a unique set of non-adrenergic high affinity binding sites for a number of agents that to date also bind to $\alpha_2$-adrenergic receptors (Eglen, R. M. et al., 1998, Trends in Pharmacol. Sci. 19: 381–390; Regunathan, S. and Reis, D. J., 1996, Ann. Rev. Pharmacol. Toxicol. 36:511–44). Although membrane-bound imidazoline receptors have not yet been cloned, evidence including differences in selectivity and binding affinity of ligands, the structure of binding proteins and cellular distribution indicate that they are different from $\alpha_2$-adrenergic receptors. The nonadrenergic imidazoline receptors are important in mediating the hypotensive actions of clinically important imidazoline drugs such as clonidine, rilmenidine and moxonidine.

For example, unique imidazoline receptors, are present in pancreatic islet and beta-cells (Morgan, N. G., et al., 1995, Ann. N.Y. Acad. Sci. 763: 361–373). Activation of these receptors by imidazolines causes release of insulin. Much of this activity is due to imidazoline-induced closure of $K^+$ channels such as the $K^+$ ATP-sensitive channels which permits intracellular levels of $K^+$ to accumulate, causing cell depolarization and eventual exocytosis of hormone or transmitter into plasma or extracellular fluid. It is noteworthy that channels such as the $K^+$ ATP-sensitive channels exist throughout the body, and are particularly abundant in brain. These pancreatic imidazoline receptors have recently been designated as I3 receptor subtypes (Eglen, R. M. et al., 1998, TIPS 19: 381–390). Chan et al. (1997, Brit. J. Pharmacol. 120: 926–932), showed that imidazolines and preparations of CDS (clonidine-displacing substance, see below) from bovine brain caused release of insulin and stimulated $K^+$ ATP channels.

One or more endogenous ligands selectively bind to the imidazoline receptors although attempts to identify this endogenous ligand(s) has failed. A possible ligand, referred to as "clonidine displacing substance" (CDS), has been discovered as an entity isolated from mammalian brain and the periphery that is capable of displacing radio-labeled clonidine and its radio-labeled congeners from membranes (Atlas, D. et al., 1987, J. Cardiovascular Pharmacology 10(Suppl. 12): S122–S127; Atlas, D. 1991, Biochemical Pharmacology 41: 1541–1549; Atlas, D., 1995, Annals of the New York Academy of Sciences 763:314–324). Antibodies have been prepared against the drug clonidine, which presumably interact with CDS. Such antibodies are found to be immunoreactive in tissues throughout the body and also show a heterogeneous regional distribution within the brain.

A recent study proposed that agmatine, a known compound isolated from bovine brain, is CDS (Li, G. et al., 1994, Science 263:966–968; Regunathan, S. and Reis, D. J., 1996, Ann. Rev. Pharmacol. Toxicol. 36: 511–544; but see Eglen, R. M. et al., 1998, TIPS 19: 381–390). Agmatine was further suggested to be an endogenous neurotransmitter because it was found within an extract of CDS activity from whole brain and because it appeared to bind to a class of imidazoline receptors. However, comparisons of the biological activities of agmatine, e.g., effects on blood pressure versus effects of endogenous clonidine-displacing substance at imidazoline and $\alpha_2$-adrenergic receptors produced in virtually all laboratories indicated that agmatine differed from "classical CDS." For example, agmatine displaces labeled clonidine from a subset of its nonadrenergic binding sites identified as imidazoline $2_A$ and $2_B$ sites. However, because those $I_{2A}$ and $I_{2B}$ sites are now known to be enzymes, i.e. portions of monoamine oxidase A and B, the search for the identity of CDS that acts at membrane-bound imidazoline receptors has continued (Eglen, R. M. et al., 1998, TIPS 19: 381–390).

Several laboratories have harvested CDS and most preparations show similar physiochemical properties. There is widespread consensus that CDS is present in small amounts in the brain, cerebrospinal fluid and periphery (including plasma) of mammals. It is soluble in water and methanol, but generally insoluble in organic solvents. Size exclusion chromatography indicated that it is a small molecule ($\leq 1000$ Da). CDS is resistant to several proteases, including trypsin and chymotrypsin, and is devoid of amino acids; thus it is not a peptide. CDS appears to have no free amino groups as activity is retained following reaction with fluorescamine and ninhydrin. CDS is stable in both weak acids (pH 2) and weak bases (pH 10.5), is thermostable (at 110° C.) and retains activity following multiple freeze-thaw and lyophilization cycles. Because CDS can be retained on both anion and cation exchange resins and because its migration patterns shifted markedly with changes in ambient pH on gel electrophoresis, it is very likely that CDS is amphoteric, possibly a zwitterion. In addition, CDS shows maximal UV absorbance between 206–220 nm.

3. SUMMARY OF THE INVENTION

The present invention relates to methods and compositions for regulating the activity of imidazoline receptors. Specifically, the invention relates to compositions comprising imidazoleacetic acid-ribotide (IAA-RP) which binds with high affinity to at least 2 subsets of imidazoline receptors, imidazoleacetic acid-riboside (IAA-R) which binds with a slightly lower affinity, and to its related congeners. As demonstrated herein, IAA-RP binds to imidazoline receptors and in one case stimulates well defined receptor-mediated signal transduction events such as release of arachidonic acid. Further, the release of arachidonic acid, an imidazoline $I_1$-receptor mediated event, is inhibited in the presence of the imidazoline $I_1$ receptor antagonist efaroxan. The discovery that IAA-RP and IAA-R bind to imidazoline receptors provides new targets for therapeutic methods aimed at amelioration of imidazoline system related disorders.

The present invention includes pharmaceutical compositions comprising IAA-RP, IAA-R, derivatives and analogs thereof, which can be utilized to regulate the activity of imidazoline and imidazoline-like receptors. Such compositions can be utilized to treat disorders related to the imidazoline system such as hypertension, glaucoma, psychiatric (e.g. depression), neurological (e.g. motor disorders, neurodegenerative disorders), diabetes and disorders involving platelet aggregation.

The invention further provides for antibodies to IAA-RP and IAA-R. Such antibodies can be utilized to ameliorate symptoms associated with imidazoline system-related disorders. For example, in the case of an anti-IAA-RP antibody, such an antibody would specifically bind to IAA-RP and possibly disrupt the ability of IAA-RP to bind to imidazoline receptors thereby preventing receptor mediated signal transduction events. Additionally, anti-IAA-RP and anti-IAA-R antibodies can be used as diagnostic and prognostic indicators of imidazoline system related disorders. For example, diagnostic methods can be utilized to detect abnormalities in the levels or tissue distribution of IAA-RP and/or IAA-R relative to normal levels. The antibodies of the invention can also be used in screening methods for detection of a predisposition to imidazoline system based disorders in an individual.

The invention further relates to methods for identification of compounds which promote or antagonize signal transduction events stimulated by the binding of IAA-RP or IAA-R to imidazoline receptors. Such compounds can act as therapeutic agents in the amelioration of a wide range of imidazoline system based disorders. The invention further relates to methods for identification of compounds that regulate the synthesis, or degradation of IAA-RP or IAA-R.

Finally, the invention relates to treatment of imidazoline based disorders, such as for example, hypertension, glaucoma, psychiatric (e.g. depression), neurological (e.g. motor disorders, neurodegenerative disorders), diabetes and disorders involving platelet aggregation by administering compositions comprising IAA-RP, IAA-R, or compounds that promote or antagonize IAA-RP or IAA-R activity.

5. DETAILED DESCRIPTION OF THE INVENTION

The present invention relates to pharmaceutical compositions comprising imidazoleacetic acid-ribotide (IAA-RP), imidazoleacetic acid-riboside (IAA-R) and their related congeners for use in regulating the activities of imidazoline receptors. The invention is based on the discovery that IAA-RP and to a lesser extent, IAA-R have significant affinities for imidazoline receptors. Further, binding of IAA-RP to the imidazoline $I_1$ receptor in the adrenal medulla stimulates release of arachidonic acid (AA), an imidazoline $I_1$ receptor-mediated signal transduction response. The release of arachidonic acid is inhibited in the presence of efaroxan, a known antagonist of the imidazoline $I_1$ receptor.

The invention encompasses compositions comprising IAA-RP, IAA-R and/or related congeners which can be utilized to regulate activities of imidazoline receptors. The invention further provides for antibodies to IAA-RP and IAA-R. Such antibodies can be utilized to ameliorate imidazoline related disorders. Alternatively, anti-IAA-RP and anti-IAA-R antibodies can be used diagnostically and prognostically to detect abnormalities in levels or tissue distribution of IAA-RP and/or IAA-R relative to normal levels.

The discovery that IAA-RP, IAA-R and related congeners bind to imidazoline receptors provides a new target for therapeutic methods aimed at amelioration of imidazoline system related disorders. Thus, the invention further relates to methods for identification of compounds which promote or antagonize the biological activity stimulated by IAA-RP, IAA-R and related congeners that bind to imidazoline receptors. Such compounds can act as therapeutic agents in the amelioration of a wide range of imidazoline based disorders.

Finally, the invention relates to treatment of imidazoline system based disorders, such as hypertension, glaucoma, psychiatric (e.g. depression), neurological (e.g. motor disorders, neurodegenerative disorders), diabetes and disorders involving platelet aggregation by administering compositions comprising IAA-RP, IAA-R, related congeners, and/or compounds that promote or antagonize IAA-RP or IAA-R activity.

Figure 1:
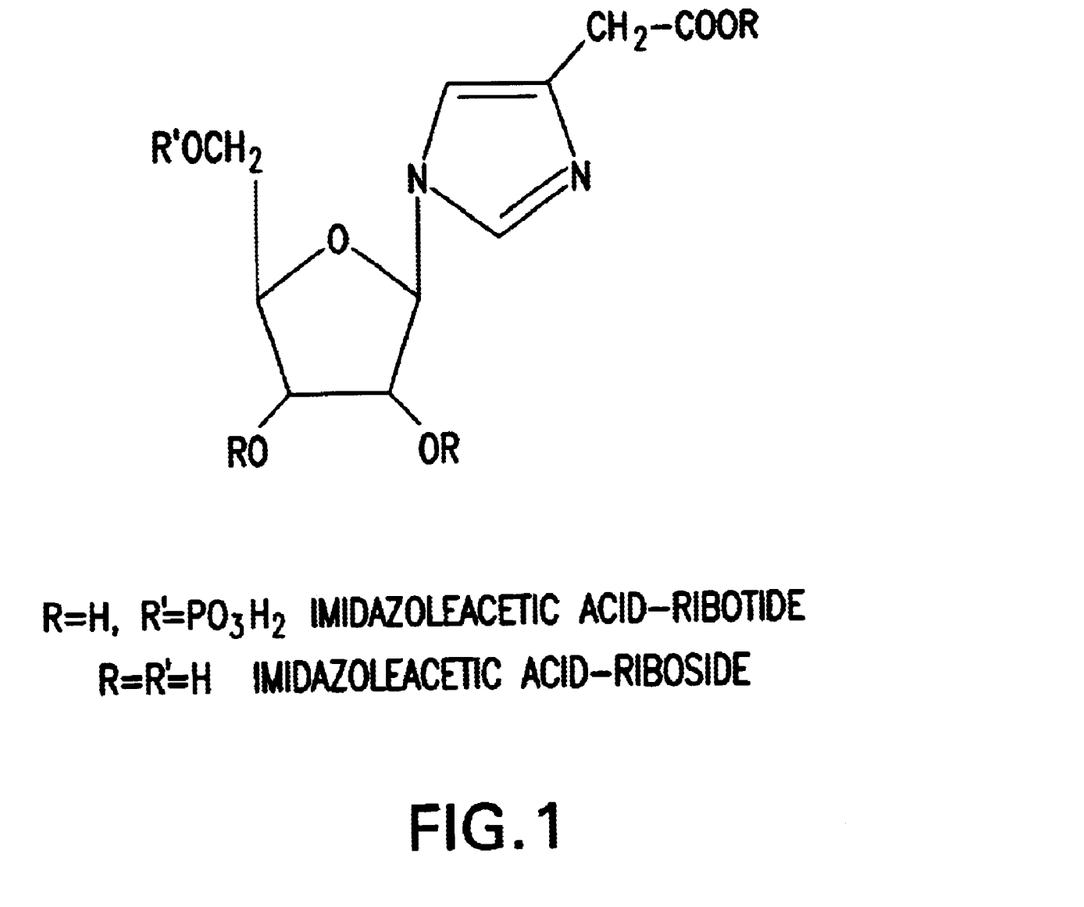
FIG. 1. Chemical structures of IAA-RP and IAA-R.

5.1. Pharmaceutical Compositions Containing IAA-RP, IAA-RP and Their Related Congeners The present invention provides pharmaceutical compositions containing imidazoleacetic acid ribotide (IAA-RP) or imidazoleacetic acid riboside (IAA-R). FIG. 1 depicts the tele-linked isomers of IAA-RP and IAA-R. IAA-RP, or tele-linked IAA-RP, is also known as imidazole-4-acetic acid-ribotide as well as 1-($\beta$-D-ribofuranosyl)-imidazole-4-acetic acid 5' phosphate. Its metabolite, IAA-R or tele-linked IAA-R, is also known as imidazole-4-acetic acid-riboside or as 1-($\beta$-D-ribofuranosyl)-imidazole-4-acetic acid. Both compounds exhibit covalent imidazole-furan linkage with the imidazole nitrogen atom furthest from the methylene-carboxy side chain. This atom is termed the tele-N or $N^\tau$, analogous to the IUPAC terms used to define the nitrogen atoms of histidine. The corresponding pros-linked isomers of IAA-RP and IAA-R, are termed 1-($\beta$-D-ribofuranosyl)-imidazole-5-acetic acid 5' phosphate or pros-linked IAA-RP and 1-($\beta$-D-ribofuranosyl)-imidazole-5-acetic acid or pros-linked IAA-R, respectively. For these compounds, the imidazole-furan linkage is with the pros-N or $N^\pi$, i.e., the imidazole ring nitrogen closest to the methylene-carboxy side chain.

In addition, pharmaceutical compositions comprising congeners and derivatives of IAA-RP and IAA-R which have a high affinity for imidazoline receptors are within the scope of the present invention. As referred to herein, congeners are defined as chemical compounds closely related to another in structure and exerting similar or antagonistic effects. For example, a structural isomer of IAA-RP with, for example, the addition of one or more phosphate or phosphonate groups. In general, the invention comprises ribosylated imidazoles, such as imidazole-furanosyl ribotides and ribosides, including but not limited to compounds such as 5-amino-4-imidazole carboxamide-ribosephosphate (AICARP, also commonly abbreviated ZMP), an intermediate in the de novo synthesis pathway of purine nucleotides. In addition, substitution of a methylene group (—$CH_2$—) for the oxygen atom that links the 5' carbon to the phosphate atom in IAA-RP, can be done to produce a molecule that is much more resistant to enzymatic dephosphorylation by phosphatases or 5' nucleases. Such molecules would have more desirable pharmacokinetic properties. In addition, 2' or 3' deoxy-IAA-RP which retain affinity for the imidazoline receptor are within the scope of the present invention. Compounds within the scope of the invention also include esters of IAA-RP, such as carboxy-methyl or carboxy-ethyl esters of IAA-RP. Such compounds are more lipid soluble, and thus, would diffuse more rapidly across biological barriers such as the blood-brain barrier or cells lining the gut.

Additionally, molecules within the scope of the invention include those compounds with linkage of the furan to the number 2 carbon atom of the imidazole ring, i.e, the carbon atom in between the two imidazole ring nitrogens. Alternatively, the furan ring may be linked to the number 2 carbon atom of the imidazole ring, with reduction of the double bond between carbons 4 and 5, leading to the conversion of the imidazole ring to an imidazoline ring or an imidazoline-like ring.

Methods for synthesis of IAA-RP and IAA-R are well known to those of skill in the art and include both biosynthetic and organic methods of synthesis. Methods for recovery and purification of IAA-RP and IAA-R from biological samples are described in various references (Karjala, S. A., 1955, J. Amer. Chem. Soc. 77:504–505; Tabor, H. and Hayaishi, O., 1955, J. Amer. Chem. Soc. 77:505–506: Crowley, G. M., 1964, J. Biol. Chem. 239: 2593–260 1; Karjala, S. A. et al., 1956, J. Biol. Chem. 219:9–12; Beaven, M. A. et al., 1974, Europ. J. Pharmacol. 29:138–146; Moss, J. et al., 1976, J. Clin. Invest. 58:137–141; Robinson, J. D. and Green, J. P., 1964, Nature 203:1178–1179; Beaven, M. A. et al., 1976, Experientia 32:1180–1182; Thomas, B. and Prell, G. D., 1993, Soc. Neurosci. Abst. 19:85; Thomas, B. and Prell, G. D., 1995, J. Neurochem. 65: 818–826; Thomas, B. et al., 1995, Soc. Neurosci. Abst. 21: 1857).

In addition, organic synthesis of IAA-R can be carried out using the method of Bauer (1958, BBA 30:219; and 1962, J. Org. Chem. 27: 167–170; Baddiley, J. et al, 1958, J. Chem. Soc. 3743–3745 ). The 5' hydroxyl group on IAA-R can be phosphorylated as presented in Matulic'-Adamic', J. and Watanabe, K. A. (1991, Korean J. Med. Chem. 1:54–64) to yield IAA-RP. In addition, IAA-RP can be enzymatically synthesized from IAA-R using for example, enzymes such as adenosine kinase (ATP:adenosine 5' phosphotransferase) to transfer a terminal phosphate from ATP to IAA-R, to produce IAA-RP. The resultant IAA-RP can be rapidly purified using any of a variety of methods including anion exchange, HPLC and TLC. Some other congeners of tele-linked IAA-RP and IAA-R (including synthesis of pros-linked IAA-RP and IAA-R) (FIG. 1) are described elsewhere (e.g. Matulic'-Adamic', J. and Watanabe, K. A., 1991, Korean J. Med. Chem. 1: 54–64).

In some instances it may be advantageous to transfer a labeled terminal phosphate from ATP to IAA-R to produce labeled IAA-RP, i.e., IAA-R$^{32}$ P. Such labeled IAA-RP will have a number of different uses including use in binding and receptor studies, during screens developed for identification of compounds having an affinity for imidazoline receptors, for isolation of imidazoline receptors as well as for analysis of the binding domains of imidazoline receptors. In addition, labeled IAA-RP can be used in pulse-chase studies of IAA-RP metabolism, analysis of IAA-RP's pharmacokinetic properties, and analysis of IAA-RP recovery in analytical methods.

To determine whether the tele- or pros- form of IAA-RP and IAA-R is present in the brain, pulse-chase experiments involving the administration of radiolabeled precursor produce IAA-RP and IAA-R were done. Using an anion-exchange HPLC/UV method we were able to separate imidazole-4-acetic acid-ribotide from imidazole-5-acetic acid-ribotide; it was determined that IAA-RP is present in rat brain, human brain, cerebrospinal fluid and preparations of CDS harvested from bovine brains. Only imidazole-4-acetic acid-ribotide, i.e., the isomer in which the furan ring is linked to the imidazole tele-nitrogen (the nitrogen located furthest from the $CH_2COOH$ side chain; see, FIG. 1) was consistently observed. Furthermore, HPLC analysis of biological samples mixed with authentic tele-linked IAA-RP prepared by organic synthesis, produced a larger UV absorption peak coincident with the tele-linked IAA-RP retention time. No split peaks or additional peaks were observed in this region of the HPLC chromatogram.

In contrast, mixing parallel biological aliquots with authentic imidazole-5-acetic acid-ribotide, i.e., the isomer in which the furan ring is linked to the pros or π ring nitrogen (the imidazole ring nitrogen located closest to the —$CH_2COOH$ side chain) produced a novel nonphysiological peak where previously there had been essentially baseline absorbance. This new peak was approximately 2 minutes behind the endogenous IAA-RP peak, a shift in retention virtually identical to that observed for I-5-AA-RP when authentic I-4-AA-RP and I-5-AA-RP were analyzed alone or together. Thus, there appears to be little or no I-5-AA-RP in the biological material we analyzed. These observations are consistent with observations made using gas chromatography-mass spectrometry where the tele-linked IAA-riboside, but not pros-linked IAA-riboside, was present in biological samples including rat brain. In addition, only the tele-linked isomer of IAA-RP shows significant activity for displacing clonidine from its nonadrenergic membrane binding sites in the adrenal medulla. The pros-linked IAA-RP isomer was devoid of this activity.

The fact that pros-linked IAA-RP or pros-linked IAA-R does not seem to be present in samples of rat brain nevertheless suggest a number of uses of pros-linked IAA-RP. For example, pros-linked IAA-RP, or pros-linked IAA-R, can be used as an internal standard in analytical techniques such as for example, in HPLC methods, to determine recovery of endogenous tele-linked IAA-RP. The pros-linked IAA-RP can also be used as a control substance when the activities of the endogenous tele-linked IAA-RP are to be assessed. More importantly, in cases such as with imidazoline $I_3$ or $I_3$-like receptors, pros-linked IAA-R has its own activities on insulin release and interactions with potassium channels.

The pharmaceutical compositions of the invention comprise an effective amount of IAA-RP, IAA-R, or related congeners and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such pharmaceutical compositions will contain a therapeutically effective amount of IAA-RP, IAA-R, and/or a related congener, preferably in purified form, together with a suitable amount of carrier so as to provide the form for proper administration to the patient. The formulation should suit the mode of administration.

5.2 Generation of Antibodies to IAA-RP, IAA-R or Related Congeners

According to the invention, IAA-RP, IAA-R or related congeners may be used as immunogens to generate antibodies which immunospecifically bind such immunogens. Such antibodies include, but are not limited to polyclonal, monoclonal, chimeric, single chain, Fab fragments, and Fab expression library.

Various procedures known in the art may be used for the production of polyclonal antibodies to IAA-RP or IAA-R or derivatives or analogs thereof. In a particular embodiment, rabbit polyclonal antibodies to an epitope of IAA-RP or IAA-R can be obtained. For the production of antibody, various host animals can be immunized by injection with IAA-RP or IAA-R, or a synthetic version, or derivative thereof, including but not limited to rabbits, mice, rats, etc. Various adjuvants may be used to increase the immunological response, depending on the host species, and including, but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward IAA-RP or IAA-R or analogs thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV hybridoma technique to produce human monoclonal antibodies (Cole et al., 1985, in Monoclonal Antibodies and Cancer Therapy, Alan R. Liss, Inc., pp. 77–96). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) can be used; such antibodies are within the scope of this invention.

In the production of antibodies, screening for the desired antibody can be accomplished by techniques known in the art, e.g., ELISA (enzyme-linked immunosorbent assay). Various immunoassays known in the art can be used to determine the binding characteristics of the antibodies, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), IAA-RP or IAA-R precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The foregoing antibodies can be used in methods known in the art relating to the localization and activity, e.g., for imaging IAA-RP and IAA-R molecules, measuring levels thereof in appropriate physiological samples, in diagnostic methods, etc. In another embodiment of the invention, anti-IAA-RP or anti-IAA-R antibodies and fragments thereof containing the binding domain can be used to regulate the activity of imidazoline receptors.

5.3. Diagnosis and Screening

Anti-IAA-RP and -IAA-R antibodies, have uses in diagnostics. Such molecules can be used in assays, such as immunoassays, to detect, prognose, diagnose, or monitor various conditions, diseases, and disorders affecting the imidazoline system. In particular, such an immunoassay is carried out by a method comprising contacting a sample derived from a patient with an anti-IAA-RP or anti-IAA-R antibody under conditions such that immunospecific binding can occur, and detecting or measuring the amount of any immunospecific binding by the antibody. In a specific aspect, such binding of antibody, in samples derived from the patient, can be used to detect aberrant IAA-RP or IAA-R localization or aberrant (e.g., high, low or absent) levels of IAA-RP or IAA-R. In a specific embodiment, antibody to IAA-RP or IAA-R can be used to assay in a patient tissue or serum sample for the presence of IAA-RP or IAA-R where an aberrant level of IAA-RP or IAA-R is an indication of a diseased condition. By "aberrant levels," is meant increased or decreased levels relative to that present, or a standard level representing that present, in an analogous sample from a portion of the body or from a subject not having the disorder.

The immunoassays which can be used, include but are not limited to, competitive and noncompetitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

Kits for diagnostic use are also provided that comprise in one or more containers an anti-IAA-RP or IAA-R antibody, and, optionally, a labeled binding partner to the antibody. Alternatively, the anti-IAA-RP or IAA-R antibody can be labeled (with a detectable marker, e.g., a chemiluminescent, enzymatic, fluorescent, or radioactive moiety).

5.4. Screening for Agonists and Antagonists of IAA-RP, IAA-R and Related Congeners A variety of different assay systems can be designed and used to identify compounds or compositions that modulate IAA-RP or IAA-R activity, and therefore, may be useful to regulate imidazoline receptors and useful in the treatment of diseases associated with the imidazoline system.

In accordance with the invention, cell-based assay systems are used to screen for compounds that modulate the activity of IAA-RP and IAA-R and thereby modulate the activity of imidazoline receptors. Compounds that may affect IAA-RP and/or IAA-R activity include, but are not limited to compounds that promote (agonists) or block (antagonists) activation of imidazoline receptors.

To this end, cells that endogenously express imidazoline receptors can be used to screen for compounds that modulate IAA-RP or IAA-R activity. Cells that express imidazoline receptors can be further engineered to incorporate a reporter molecule, the expression of which is linked to the signal transduced by IAA-RP or IAA-R or related congener activation of imidazoline receptors to aid in identification of compounds that modulate activity. Cells to be used to screen for compounds are cells that respond to activation of imidazoline receptors by IAA-RP, or IAA-R, or their congeners, e.g., as measured by a chemical, physiological, biological, or phenotypic change. For example, a test compound may be used to assess the ability for IAA-RP, IAA-R or a related congener to bind to imidazoline receptors and thereby inhibit or activate signal transduction processes. In one case, release of arachidonic acid can be used to assess imidazoline $I_1$ activity. In addition, release of insulin and/or closure of $K^+$ ATP channels can be used to assess imidazoline $I_3$ activity.

In utilizing such cell-based assay systems, cells that express imidazoline receptors are exposed to a test compound or to vehicle controls (e.g., placebos). After exposure, the cells can be assayed to measure the expression and/or activity of components of the signal transduction pathway affected by IAA-RP, IAA-R or their congeners. For example, in cells of the adrenal medulla that express imidazoline $I_1$ receptors, binding of IAA-RP and IAA-R are associated with release of arachidonic acid; thus, in a specific embodiment of the invention, assays may be designed to measure arachidonic acid. The ability of a test compound to decrease levels of arachidonic acid release, as compared to those levels seen with cells treated with a vehicle control, indicates that the test compound inhibits signal transduction mediated by binding of IAA-RP, IAA-R or a related congener to an imidazoline $I_1$ receptor. In addition, assays may be developed to measure IAA-RP or IAA-R induced release of insulin from pancreatic β-cells or release of catecholamines from chromaffin cells.

Non-cell based assays may be used to identify compounds that bind to IAA-RP or IAA-R molecules. The principle of assays used to identify compounds that bind to IAA-RP or IAA-R involves preparing a reaction mixture of the molecules and the test compound under conditions and for time sufficient to allow the two components to interact and bind, thus forming a complex which can be removed and/or detected in the reaction mixture. The identity of the bound test compound is then determined.

The screening assays are accomplished by any of a variety of commonly known methods. For example, one method to conduct such an assay involves anchoring the IAA-RP, IAA-R, or a related congener onto a solid phase and detecting IAA-RP or IAA-R/test compound complexes retained on the solid phase at the end of the reaction. In one embodiment of such a method, the IAA-RP or IAA-R reactant is anchored onto a solid surface, and the test compound, which is not anchored, may be labeled, either directly or indirectly.

In practice, microtitre plates can be utilized conveniently as the solid phase. The anchored component is immobilized by non-covalent or covalent attachments. The surfaces may be prepared in advance and stored. In order to conduct the assay, the non-immobilized component is added to the coated surfaces containing the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the solid surface; e.g., using a labeled antibody specific for the previously non-immobilized component.

Alternatively, a reaction is conducted in a liquid phase, the reaction products separated from unreacted components using an immobilized antibody specific for IAA-RP, IAA-R, or a related congener, fusion protein or the test compound, and complexes detected using a labeled antibody specific for the other component of the possible complex to detect anchored complexes.

Assay for compounds that interfere with the interaction of IAA-RP, IAA-R, or related congeners with imidazoline receptors can be performed. Ligand/receptor interactions can be detected at the end of the reaction comparing interactions in the presence or absence of test compound. The order of addition of test compounds can be varied to obtain different information about the compounds being tested. For example, test compounds that interfere with the interaction by competition can be identified by conducting the reaction in the presence of the test compound, i.e., by adding the test compounds to the reaction mixture prior to or simultaneously with IAA-RP, IAA-R, or a related congener. Alternatively, test compounds that disrupt preformed complexes, i.e, those compounds with higher binding constants that displace one of the components from the complex, can be tested by adding the test compound to the reaction after the complexes have formed.

In addition, assays may be used to identify compounds that interfere with the expression or degradation of IAA-RP or IAA-R. For example, IAA-RP is synthesized by imidazoleacetic acid phosphoribosyltransferase (IPRT) (Thomas, B. and Prell, G. D., 1995, J. Neurochem. 65:818–826). In an embodiment of the present invention, assays may be developed to identify compounds which inhibit IPRT thereby reducing levels of IAA-RP and/or IAA-R. Alternatively, such assays may be used to identify compounds that activate IPRT resulting in elevated levels of IAA-RP and/or IAA-R. In a non-limiting embodiment of the invention, antibodies directed against IAA-RP or IAA-R may be used in the assays of the invention to detect changes in levels of IAA-RP and/or IAA-R.

IAA-RP is metabolized to IAA-R by dephosphorylation through the action of either 5' phosphatases and/or 5' nucleotidases (endo or ecto). Inhibition of such phosphatases or nucleotidases would result-in accumulation of IAA-RP and/or reductions in levels of IAA-RP. Alternatively, activation of such phosphatases and/or nucleotidases would result in reduction in levels of IAA-RP and/or an increase in levels of IAA-R. In yet another embodiment of the invention, assays may be developed to identify compounds capable of regulating the activity of 5' phosphatases and/or 5' nucleotidases.

The compounds which may be screened in accordance with the invention include, but are not limited to inorganic compounds, peptides, antibodies and fragments thereof, and other organic compounds (e.g., peptidomimetics) that bind to imidazoline receptors and either mimic the activity of IAA-RP, IAA-R or a related congener (i.e., agonists) or inhibit the activity of IAA-RP, IAA-R (i.e., antagonists). Compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to, members of random or partially degenerate directed phosphopeptide libraries; see, e.g., Songyang, Z. et. al., 1993, Cell 72:767–778).

5.5. Treatment and Prevention of Disorders Involving the Imidazoline System

Diseases and disorders involving imidazoline receptors are treated or prevented by administration of a compound that either promotes or antagonizes the activity stimulated by binding of IAA-RP, IAA-R or a related congener to imidazoline receptors.

In specific embodiments, compositions that promote IAA-RP or IAA-R function are administered to an individual: (1) in diseases or disorders involving an absence or decreased (relative to normal or desired) level of IAA-RP or IAA-R, for example, in patients where the IAA-RP or IAA-R are lacking, biologically inactive or underactive, or under expressed; or (2) in diseases or disorders wherein in vitro (or in vivo) assays indicate that the utility of IAA-RP, IAA-R or a related congener agonist administration. The absence or decreased level of IAA-RP or IAA-R can be readily detected, e.g., by obtaining a patient tissue sample (e.g., from biopsy tissue) and assaying levels. Many methods standard in the art can be thus employed, including but not limited to assays for biological activity (e.g. arachidonic acid, insulin, and catecholamines release), immunoassays to detect and/or visualize IAA-RP or IAA-R (e.g., Western blot, immunoprecipitation followed by sodium dodecyl sulfate polyacrylamide gel electrophoresis, immunocytochemistry, ELISA assays, etc.).

In some instances, imidazoline system-based disorders can be treated or prevented by administration of a composition that antagonizes (inhibits) IAA-RP or IAA-R function. Compounds that inhibit IAA-RP or IAA-R function can be identified by use of known convenient in vitro assays, e.g., based on their ability to inhibit binding of IAA-RP or IAA-R to imidazoline receptors. Preferably, suitable in vitro or in vivo assays are utilized to determine the effect of a specific compound and whether its administration is indicated for treatment of the affected tissue.

In specific embodiments, compounds that inhibit IAA-RP or IAA-R function are administered therapeutically (including prophylactically): (1) in diseases or disorders involving an increased (relative to normal or desired) level of IAA-RP or IAA-R; or (2) in diseases or disorders wherein in vitro (or in vivo) assays indicate the utility of IAA-RP or IAA-R antagonist administration. The increased levels in IAA-RP or IAA-R concentration and/or function can be readily detected, e.g., by quantifying levels, by obtaining a patient tissue sample (e.g., from biopsy tissue) and assaying it in vitro for levels of the molecules, and/or activity of the molecules. Many methods standard in the art can be thus employed, including but not limited to assays for detecting release of arachidonic acid (e.g. in the case of disorders affected by imidazoine $I_1$ receptors), immunoassays to detect and/or visualize IAA-RP or IAA-R (e.g., immunocytochemistry, in situ hybridization, ELISA assays, etc.).

The compositions of the invention are preferably tested in vitro, and then in vivo for the desired therapeutic or prophylactic activity, prior to use in humans. For example, in vitro assays can be used to determine whether administration of a specific compound is indicated, including in vitro cell culture assays in which a patient's tissue sample is grown in culture and exposed to the compound, and the effect of such compound upon the tissue sample is observed. For example, compositions can be tested for their ability to either stimulate or inhibit the binding of IAA-RP, IAA-R or related congeners to imidazoline receptors. Alternatively, the ability of a compound to inhibit or stimulate receptor mediated signal transduction events, such as release of arachinoic acid (in the case of $I_1$ receptors) can be tested.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.6. Administration of Pharmaceutical Compositions

Various delivery systems are known and can be used to administer the compositions of the invention, e.g. encapsulation in liposomes, microparticles, microcapsules. Methods of introduction include, but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

The amount of the compositions of the invention which may be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

IAA-RP and IAA-R Bind to the Imidazoline Receptor

In the example detailed below, binding of IAA-RP, IAA-R and related congeners to imidazoline receptors was demonstrated. In addition, IAA-RP induced the release of arachidonic acid, an imidazoline $I_1$ receptor mediated response in cultured medullary adrenal cells and the $I_1$ receptor antagonist efaroxan was found to inhibit this IAA-RP-induced release of arachidonic acid.

6.1. Materials and Methods 6.1.1. Tissue Preparation

Whole bovine brains and adrenal glands were obtained from a local slaughterhouse. Brains were immediately placed on a chilled glass plate, washed with ice-cold Krebs'-Henseleit buffer, and dissected. The rostral medulla was isolated by transecting the brainstem rostrally at the posterior margin of the trapezoid body and caudally 1 cm caudal to the obex. The pia-arachnoid was removed, and the lateral medulla was isolated by a sagittal section through the lateral margin of the pyramids, and then bisected. The ventral half was defined as the ventrolateral medulla (VLM). Brain samples were transported on ice to the laboratory and processed immediately.

Fresh bovine adrenal glands (<10 min post-mortem) were dissected free of associated fat and connective tissue and perfused retrogradely through the adrenal vein with 25 ml ice-cold Krebs'-Henseleit bicarbonate buffer. The glands were drained and reperfused with Krebs'-Henseleit buffer, drained, and then perfused again with 25 ml ice-cold Krebs'-Henseleit buffer containing 0.025% collagenase (type D, Boehinger Mannheim). The glands were incubated with occasional mixing during transport to the laboratory (about one hour), then perfused with 25 ml fresh buffer containing collagenase and incubated for 30 min at 35° C. The digested glands were split and the medulla was scraped away from the cortex and placed under 20 ml of buffer containing collagenase. Adrenal medullae were mechanically minced (Tekmar Tissueminzer, setting 40 for 30 sec) and incubated with stirring for 30 min at 37° C. The digest was filtered through stainless steel mesh and the filtrate centrifuged at 200×g for 10 min at 20° C. The cell peliet was resuspended in 30 ml Krebs' without collagenase, recentrifuged, lysed by flash-freezing, and stored overnight at −70° C. About 70% of the cells isolated in this way are chromaffin cells as shown by neutral red staining.

6.1.2 Membrane Preparation

Fresh bovine VLM was homogenized by using a polytron (Tekmar Tissuemizer, setting 80 for 2×15 sec) in 20 volumes of ice-cold Hepes-buffered isotonic sucrose (pH brought to 7.4 with Tris base) containing the protease inhibitors (1,10)-phenanthroline (100 $\mu$M) and phenylmethylsulfonyl fluoride (50 $\mu$M) in order to inhibit degradation of receptor protein. Bovine adrenomedullary cells were homogenized in 15 ml Hepes-buffered isotonic sucrose by 10 strokes in a glass-glass hand-held homogenizer. All three homogenates were centrifuged at 1000×g for 5 min at 4° C. to remove nuclei and debris. The pellets (P1) were resuspended in 20 ml of homogenization buffer, and centrifuged again at 1000×g for 5 min. The combined supernatants were centrifuged at 48,000 g for 18 min at 4° C., and the resulting P2 pellet was resuspended in 10 to 25 volumes of 50 mM Tris-HCl buffer (pH 7.7) containing 5 mM EDTA. After recentrifugation at 48,000 g for 18 min, the resulting membrane pellet was resuspended in Tris-HCl containing 25 mM NaCl, preincubated for 30 min at 25° C., chilled on ice, centrifuged again, resuspended a final time in Tris-HCl alone, centrifuged, flash-frozen, and stored at −70° C. for up to three months.

6.1.3. [$^3$H]Clonidine and [$^{125}$]p-iodoclonidine Binding Assays

Radioligand binding assays with [$^3$H]clonidine or [$^{125}$]p-iodoclonidine for determination of specific membrane binding to VLM and renal medulla imidazoline sites and $\alpha_2$-adrenergic receptors were performed by a modification of methods previously described (Ernsberger P. et al., 1997, J. Hypertension 1997, 15:S9–S23). Membranes were slowly thawed and resuspended in Tris-Hepes buffer (5.0 mM; pH 7.7 at 25° C., containing 0.5 mM EDTA, 0.5 mM EGTA, and 0.5 MM $MgCl_2$) at a concentration of 1 mg protein/ml for the VLM, 4 mg protein/ml for the renal medulla, and 0.2 mg protein/ml for adrenomedullary cells. Assays were conducted in a total volume of 250 $\mu$l in polypropylene 96-well plates (Beckman Macrowell), and each well contained 125 $\mu$l membrane suspension, 25 $\mu$l radioligand, and 100 $\mu$l drug or vehicle. Incubations were initiated by the addition of membrane and were carried out for 30 min at 22° C. Nonspecific binding was defined in the presence of 10 $\mu$M BDF-6143, an imidazoline adrenergic agent. Specific $\alpha_2$-adrenergic binding was defined by inhibition with (−)epinephrine (0.1 mM). In experiments using catecholamines, all samples contained ascorbic acid in a final concentration of 0.001%. Incubations were terminated by vacuum filtration using a cell harvester (Brandel) equipped with Teflon tubing to reduce absorption of the radioligand over glass fiber filters (Schleicher & Schuell #34) which were preincubated for 4 h at 4° C. in 0.03% polyethylimine to reduce nonspecific binding to the filter. The filters were washed four times with 5 ml ice-cold Tris-HCl, placed in scintillation vials, covered with 4 ml scintillation cocktail (BioSafe II, Research Products International), and counted at 50% efficiency (Beckman LS5801). Protein was assayed by the bicinchoninic acid method.

Data were obtained as dpm and transferred to the Equilibrium Binding Data Analysis (EBDA) program for initial processing; 4 to 10 experiments were analyzed simultaneously by using the LIGAND program for nonlinear curve-fitting. Protein assay data were also analyzed by nonlinear curve-fitting.

[$^3$H]Clonidine (60–80 Ci/mmol) and [$^{125}$I]p-iodoclonidine (2200 Ci/mmol) were obtained from New England Nuclear (Boston, Mass.), stored at −20° C. in ethanol and diluted in water prior to assay. Stock solutions of both compounds were made in 0.01 M acetic acid up to one week prior to use. Epinephrine and clonidine were purchased from Sigma Chemical (St. Louis, Mo.). Cimetidine was purchased from Research Biochemicals International (Natick, Mass.).

Assays for measuring imidazoline receptor-mediated arachidonic acid release from PC12 cells is as described in Ernsberger et al., (1995, FASEB J. 9:A114).

6.1.4. Preparation of Antibodies

IAA-RP linked to KLH was prepared by first reacting disodium IAA-RP (11.1 µmol) with 10 mg of 1-ethyl-3-(3-dimethylaminopropyl)carbodiimide HCl (EDCI; Sigma) in 0.5 mL of acidified saline (pH 6). After 5 min this was mixed with freshly dialyzed KLH protein (0.5 mg in 0.5 ml of 10 mM phosphate buffered saline [PBS; pH 7.4]). The solution was incubated at room temperature for 5–7 h, then dialyzed repeatedly against PBS at 4° C. Five male mice were injected (approx. 0.2 ml i.p.) with 200–250 µg KLH linked to IAA-RP prepared in Freund's Complete Adjuvant in oil. Each mouse received booster injections (i.v.) of KLH-IAA-RP in PBS after 6 weeks and 18 weeks. Five days after the last injection, the mouse with highest IAA-RP antibody titer was anesthesized with ether, then bled. Whole blood was collected, allowed to clot, then centrifuged (3000 g). The untreated plasma was the source of polyclonal antibodies against IAA-RP (pAb-IAA-RP). The mouse was euthanized by cervical dislocation then underwent spleenectomy, for preparation of monoclonal antibodies.

IAA-RP (as well as IAA-R and numerous potential congeners and related imidazoles) was similarly linked to BSA (Sigma) as was done for KLH above. After dissolving in 0.15 M NaHCO$_3$, the solution was applied (approx. 0.5 g/well) to 96 well plastic Maxisorp immunoplates (Nunc) for use in an Enzyme-Linked Immunosorbent Assay (ELISA) method. Solutions (100 µl) of pAb-IAA-RP (diluted up to 1:8000 in PBS) applied to treated ELISA plates containing bound BSA-IAA-RP were incubated for 60 min at 37° C. After washing (5 times with PBS), 100 µl of a second antibody (goat-antimouse; 1:1000 dilution in PBS/1% BSA) linked to peroxidase (Kirkegaard and Perry Labs, Inc.) was added to each well and incubated for 60 min at 37° C. After washing (5 times with PBS), 95 41 of peroxidase substrate solution, ABTS (Kirkegaard and Perry Labs, Inc.), was added to each well. Plates were incubated for 20 min-4h at 37° C. Optical density was assayed at 414 nm using a Spectra Max UV/V spectrometer as the detector system.

6.2. Results

Figure 2:
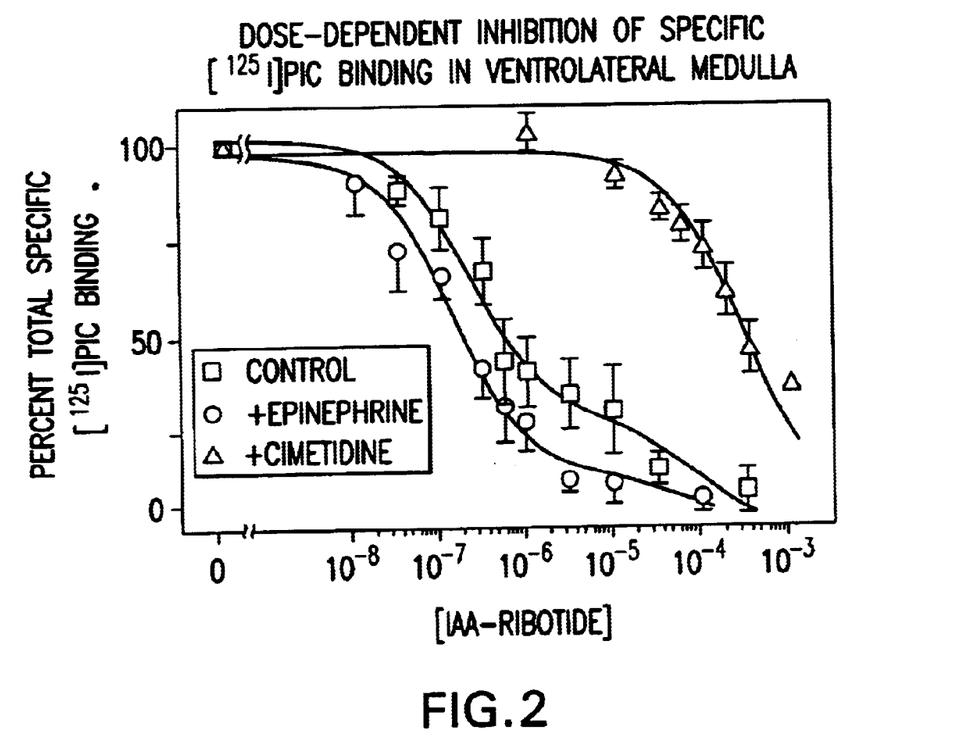
FIG. 2. IAA-RP inhibition curves after selective blockade of either $\alpha_2$-adrenergic or imidazoline receptor sites in the RVLM (Rostal Ventral lateral Medulla) of brain. Data represent the mean±S.E.M. of 4 to 6 experiments, each conducted in triplicate. VLM it membranes were incubated with increasing concentrations of IAA-RP in the presence of vehicle alone (1.0 mM acetic acid; control), with epinephrine (0.1 mM) added to mask $\alpha_2$-receptors, or with cimetidine (10 $\mu$M) added to mask imidazoline receptors. Each curve was normalized to the total specific binding under that condition. Results of curve-fitting analysis are shown in Table 2.

The data presented in FIG. 2, and Table 1 below, demonstrate that IAA-RP inhibits binding of labeled clonidine to bovine RVLM membranes.

TABLE 1

Binding parameters for IAA-RP inhibition of [$^{125}$I]p-iodoclonidine binding to bovine RVLM membranes

| Condition | Imidazoline I Sites | | $\alpha_2$-Adrenergic Sites | |
|---|---|---|---|---|
| | $K_i$ (nM) | Percent Sites | $K_i$ (µM) | Percent Sites |
| Control | 160 ± 38 | 71 ± 5 | 57 ± 33 | 29 ± 5 |
| With epinephrine | 100 ± 19 | 86 ± 4 | 60 ± 48 | 14 ± 4 |
| With cimetidine | | 0 ± 0 | 210 ± 32 | 100 ± 10 |

$K_i$ values are IAA-RP concentration in nM (imidazoline sites) or µM ($\alpha_2$-adrenergic sites)±the standard error of the estimate and were obtained by nonlinear curve-fitting to a two-component logistic equation. IAA-RP distinguished two populations of [$^{125}$I]p-iodoclonidine binding sites. Sites with a high affinity for IAA-RP represented 71% of the total sites in the control condition, increased to 86% after selective masking of $\alpha_2$-adrenergic receptors with epinephrine and were eliminated by the addition of cimetidine to mask imidazoline sites. Conversely, sites with a low affinity for IAA-RP were diminished in the presence of epinephrine, but were predominant in the presence of cimetidine. These data indicate that VLM imidazoline receptor sites have a high affinity for IAA-RP whereas, $\alpha_2$-adrenergic receptors have low affinity.

Figure 3:
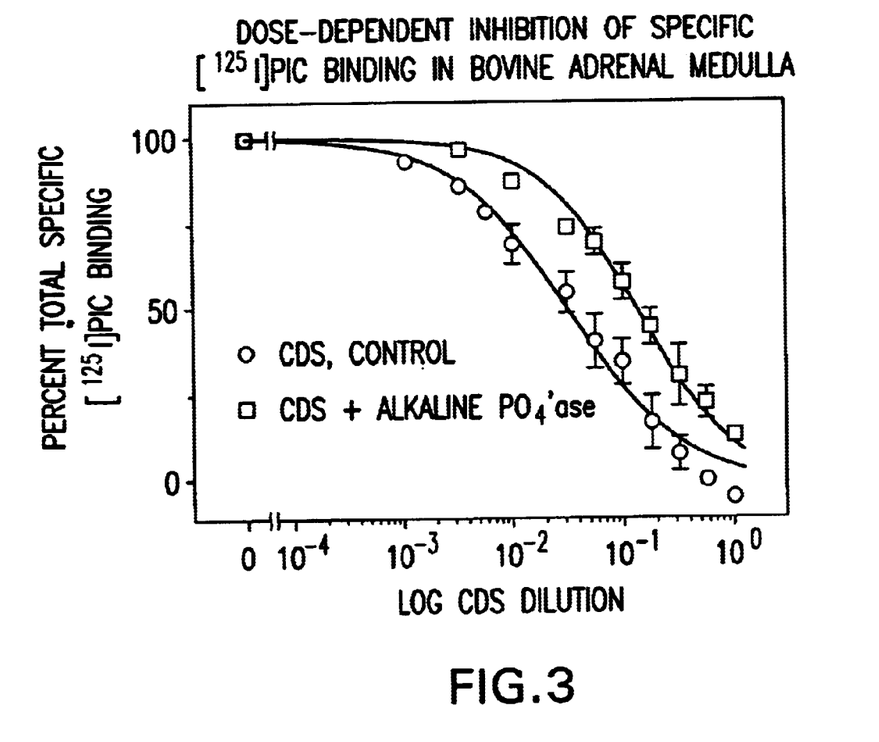
FIG. 3. Effect of phosphatase treatment on the dose-dependent inhibition of $^{125}$I-iodoclonidine binding to adrenomedullary cell membranes by brain extract containing CDS.
Figure 4:
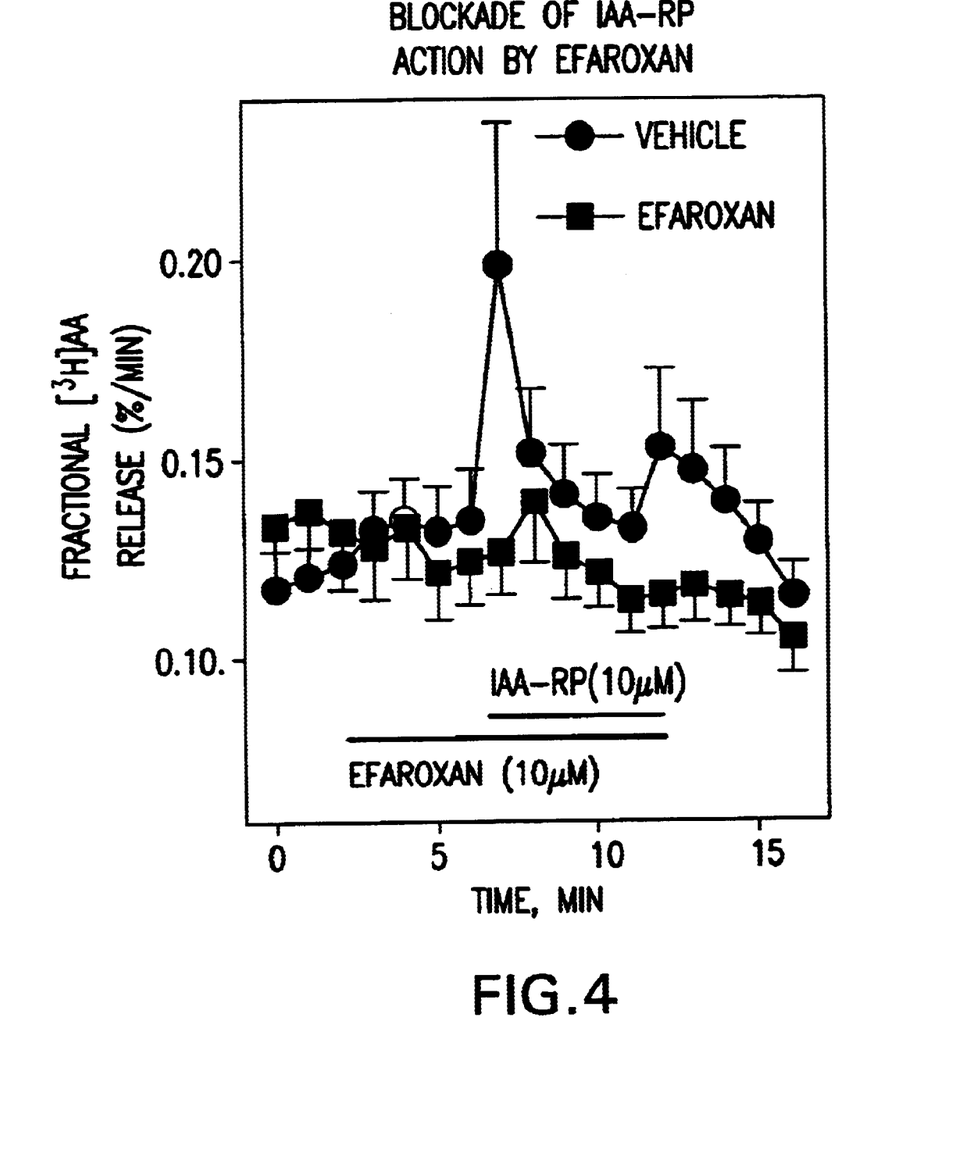
FIG. 4. Stimulation of arachidonic acid release by IAA-RP, an imidazoline $I_1$ response, and inhibition of arachidonic acid release by efaroxan an $I_1$ antagonist.

Authentic IAA-RP and IAA-R were both able to displace [$^{125}$I-]p-iodoclonidine; IAA-RP had a 3–30 fold greater affinity than IAA-R. In addition, incubation of brain-derived CDS with exogenous phosphatase reduced the binding affinity of CDS to adrenomedullary cell membranes (FIG. 3). In addition, as demonstrated in FIG. 4, CDS activity derived from bovine brain extracts and synthetic IAA-RP, each stimulated release of arachidonic acid from PC-12 cells. This effect was blocked by the selective imidazoline I$_1$ antagonist, efaroxan. In addition, CDS activity was shown to stimulate the release of catecholamines from adrenal chromaffin cells. In experiments using insulinoma cells in culture (e.g., β-TC3 cells), it was also observed that IAA-RP was capable of stimulating insulin release indicating that such cells are responsive to IAA-RP.

7. EXAMPLE

Stimulation of Insulin Release from Pancreatic Cells by IAA-RP AND IAA-R

The example described below demonstrates that IAA-RP (tele-linked) stimulated release of insulin from cultured insulinoma cells (β-TC3 cells), further indicating that IAA-RP is a CDS compound. Furthermore, it suggests a useful model system for assaying imidazoline induced changes in K$^+$ channel activity such as, for example, activation (i.e., closure) of K$^+$ ATP-sensitive channels and/or regulation of transmitter release in regions of the body other than the pancreas. Such assays provide useful model systems for studying the relationship between imidazolines, neuropsychiatric and neurodegenerative disorders, and cell pathology and death associated with potassium channel dysfunction can occur with K$^+$ ATP channels.

7.1. Materials and Methods

Islets of Langerhans from male Wistar rats were isolated by collagenase digestion in a medium of bicarbonate-buffered physiological saline solution containing 4 mM D-glucose and 1 nM CaCl$_2$. Islets were selected under a binocular dissecting microscope and were used within two hours of isolation. Islets from humans were isolated from heart-beating cadaver organ donors by collagenase digestion and density gradient centrifugation (Chan, S. L. F., et al., 1997, Brit. J. Pharmacol. 120:926–932).

Incubations were done in 96-well plates. Isolated islets were incubated in 100 µl buffer solution supplemented with bovine serum albumin in humidified air: $CO_2$ (95:5%) at 37° C. in the presence of test agents. To eliminate any potential alpha-2 responses, yohimbine (10 µM), a potent $alpha_2$-adrenergic blocker, was included in all incubations. After 60 min incubation, samples of medium were removed for measurement of insulin release by radioimmunoassay using anti-bovine insulin antiserum. Presence of insulin in the test media were compared to controls; positive differences represented amounts of insulin released. In reversal experiments, diazoxide (e.g., 200 µM) was pre-incubated to block glucose-induced insulin release. In these studies, test reagents were used to determine if they were capable of overcoming diazoxide's inhibitory effects on $K^+$ ATP channels, a well known action of imidazoline secretagogues in islet cells. For example, efaroxan (an inhibitor of I-1 responses in adrenal medullary cells) is a well known I-3 agonist, i.e., it stimulates (at 100 µM) release of insulin and overcomes diazoxide inhibition thus illustrating again the dictomy between $I_1$ and $I_3$ receptor subtypes.

7.2 Results

The tele-isomers of IAA-RP and IAA-R (FIG. 1) and some of its congeners were evaluated in isolated pancreatic beta-cells harvested from normal rats and humans after autopsy. In direct stimulation experiments in rats, the tele-isomers of IAA-RP and IAA-R were potent stimulants of insulin release; the magnitude of response was dose-dependent, oftentimes effective at concentrations as low as 10 µM. The pros-isomer of IAA-R likewise stimulated insulin release with effects similar to or even greater than that seen with tele IAA-RP. Furthermore, tele-linked IAA-RP and tele- and pros-IAA-R were each able to reverse the inhibitory action of diazoxide on glucose-induced insulin release.

Diazoxide opens ATP-sensitive $K^+$ channels; a common feature of imidazolines active at $K^+$ channels (in particular, pancreatic $I_3$ receptors) is that such imidazolines reverse effects of diazoxide (Morgan, N. G., et al., 1995, Ann. N.Y. Acad. Sci. 763: 361–373; Chan, S. L. F., et al., 1997, Brit. J. Pharmacol. 120: 926–932).

As demonstrated, the imidazoleacetic acid-linked ribotides and ribosides are potent stimulants at yet another group of imidazoline receptors, the $I_3$ subtypes. The $I_3$ subtypes are associated with $K^+$ ATP-sensitive channels, and the latter are present in many tissues of the body, particularly in the brain. Since IAA-RP immunoreactive cells are particularly rich in selected regions of the brain (e.g., particularly in the RVLM region of the brainstem), it is likely that the imidazole-linked ribotides and ribosides and their congeners also affect $K^+$ channels, for example $K^+$-AT$\beta$-sensitive channels, present in nervous tissue. Such localization in the VLM again confirms that IAA-RP is a CDS.

The present invention is not to be limit in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

I claim:

1. A method for activating an imidazoline receptor expressed in a cell comprising contacting said cell with an imidazoleacetic acid-ribotide.

2. A method for activating an imidazoline receptor expressed in a cell comprising contacting said cell with an imidazoleacetic acid-riboside.

3. The method of claim 1 or 2 wherein the methylene group is substituted for the oxygen atom that links the 5' carbon to the phosphate atom in the imidazoleacetic acid-ribotide.

4. The method of claim 1 or 2 wherein the imidazoleacetic acid-ribotide is a 2' or 3' deoxy-IAA-RP.

5. The method of claim 1 or 2 wherein the imidazoleacetic acid-ribotide is a carboxy-methyl or carboxy-ethyl ester of IAA-RP.

6. The method of claim 1 or 2 wherein furan is linked to the number 2 carbon atom of the imadazole ring.

7. The method of claim 1 or 2 wherein furan is linked to the nitrogen closest to the methylene-carboxy side chain of the imidazole ring.

8. The method of claim 1 or 2 wherein the imadazole ring is converted to an imadzoline ring.

9. The method of claim 1 or 2 wherein the activation of the imidazoline receptor results in release of arachidonic acid from said cell.

10. The method of claim 1 or 2 wherein the activation of the imidazoline receptor results in release of insulin from said cell.

11. The method of claim 1 or 2 wherein the activation of the imidazoline receptor results in release of catecholamines from said cell.

* * * * *